United States Patent
Pressly et al.

(10) Patent No.: US 9,597,273 B2
(45) Date of Patent: Mar. 21, 2017

(54) METHODS FOR TREATING RELAXED HAIR

(71) Applicant: Liqwd, Inc., Santa Barbara, CA (US)

(72) Inventors: Eric D. Pressly, Santa Barbara, CA (US); Craig J. Hawker, Santa Barbara, CA (US)

(73) Assignee: Liqwd, Inc., Santa Barbara, CA (US)

( * ) Notice: Subject to any disclaimer, the term of this patent is extended or adjusted under 35 U.S.C. 154(b) by 0 days.

(21) Appl. No.: 15/137,788

(22) Filed: Apr. 25, 2016

(65) Prior Publication Data

US 2016/0310394 A1    Oct. 27, 2016

Related U.S. Application Data

(60) Provisional application No. 62/152,220, filed on Apr. 24, 2015.

(51) Int. Cl.

| | | |
|---|---|---|
| *A61K 8/46* | (2006.01) | |
| *A61K 8/19* | (2006.01) | |
| *A61K 8/36* | (2006.01) | |
| *A61K 8/362* | (2006.01) | |
| *A61K 8/41* | (2006.01) | |
| *A45D 7/04* | (2006.01) | |
| *A61Q 5/04* | (2006.01) | |
| *A61Q 5/02* | (2006.01) | |
| *A61Q 5/12* | (2006.01) | |

(52) U.S. Cl.
CPC ............... *A61K 8/466* (2013.01); *A45D 7/04* (2013.01); *A61K 8/19* (2013.01); *A61K 8/36* (2013.01); *A61K 8/362* (2013.01); *A61K 8/41* (2013.01); *A61K 8/416* (2013.01); *A61K 8/46* (2013.01); *A61Q 5/02* (2013.01); *A61Q 5/04* (2013.01); *A61Q 5/12* (2013.01); *A61K 2800/59* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | |
|---|---|---|
| 2,850,351 A | 9/1958 | Moore et al. |
| 3,142,623 A | 7/1964 | Zviak et al. |
| 3,472,243 A | 10/1969 | Wall |
| 3,840,656 A | 10/1974 | Kalopissis et al. |
| 4,240,450 A | 12/1980 | Grollier |
| 4,425,132 A | 1/1984 | Grollier et al. |
| 4,532,950 A | 8/1985 | Lang et al. |
| 4,812,307 A | 3/1989 | Siuta-Mangano |
| 4,834,971 A | 5/1989 | Klenk |
| 5,143,518 A | 9/1992 | Madrange et al. |
| 5,221,286 A | 6/1993 | Singleton et al. |
| 5,350,572 A | 9/1994 | Savaides et al. |
| 5,565,216 A | 10/1996 | Cowsar |
| 5,656,265 A | 8/1997 | Bailey et al. |
| 5,811,085 A | 9/1998 | Halloran |
| 5,833,966 A | 11/1998 | Samain |
| 6,173,717 B1 | 1/2001 | Schonert |
| 6,458,906 B1 | 10/2002 | Torgerson et al. |
| 6,537,532 B1 | 3/2003 | Torgerson et al. |
| 6,706,258 B1 | 3/2004 | Gallagher et al. |
| 6,984,250 B1 | 1/2006 | Legrand |
| 7,041,142 B2 | 5/2006 | Chan et al. |
| 7,390,479 B2 | 6/2008 | Sockel et al. |
| 7,598,213 B2 | 10/2009 | Geary et al. |
| 8,298,519 B2 | 10/2012 | Adams et al. |
| 8,613,913 B2 | 12/2013 | Chang |
| 9,055,518 B2 | 6/2015 | Vainola |
| 9,095,518 B2 | 8/2015 | Pressly et al. |
| 9,144,537 B1 | 9/2015 | Pressly et al. |
| 9,180,086 B2 | 11/2015 | Cabourg |
| 9,326,926 B2 | 5/2016 | Pressly et al. |
| 2001/0042276 A1 | 11/2001 | Kawasoe et al. |

(Continued)

FOREIGN PATENT DOCUMENTS

| | | |
|---|---|---|
| DE | 1220969 | † 7/1966 |
| DE | 4300320 | 7/1994 |

(Continued)

OTHER PUBLICATIONS

Expert Village, Hair color mixing and aopplication techniques: Mixing bleach for highlights , https://www.youtube.com/watch?v=nOE_BaC57mw, 3 pages, retrieved from the internet May 17, 2016.

Halal, The Chemistry of Haircolor: Chemistry Simplified presentation file slide 36 , Slide presentation showing hair treatment chemistry including bis-aminopropyl diglycol dimaleate, includes slide No. 36 asking Does it work with hydroxide relaxers?, http://chemistrysimplified.com/wp-content/uploads/2015/07/CEA-2015-Chemistry-of-Haircolor.pdf (2015).

International Search Report and Written Opinion for PCT/US2016/029215 mailed Jul. 8, 2016.

International Search Report for PCT application, PCT/US2015/065032, mailed May 9, 2016.

Lab muffin "How Does Olaplex Hair Treatment Work?" http://www.labmuffin.com/2015/04/how-does-hair-treatment-work, 8 pages retrieved from the internet Jun. 24, 2016.

(Continued)

*Primary Examiner* — Abigail Fisher
(74) *Attorney, Agent, or Firm* — Pabst Patent Group LLP

(57) ABSTRACT

Methods and kits for treating hair or preventing damage in the relaxing of hair are disclosed herein. Hair that is damaged during a relaxing treatment with hydroxide-containing relaxing agents, can be treated with formulations containing one or more active agents. The active agent formulations can be applied simultaneously with the hair relaxing formulation, or optionally applied immediately following application of the relaxing formulation, to reduce damage and breakage. Use of the active agent formulation along with a relaxing treatment can be used to control the level of curl achieved or retained in the relaxed hair, as compared to the natural amount of curl in the untreated hair.

29 Claims, No Drawings

(56) References Cited

U.S. PATENT DOCUMENTS

| | | | |
|---|---|---|---|
| 2003/0049222 A1* | 3/2003 | Akhter | A45D 2/001 424/70.4 |
| 2004/0086475 A1 | 5/2004 | Boswell | |
| 2005/0087718 A1 | 4/2005 | Okada | |
| 2006/0024257 A1 | 2/2006 | Chang et al. | |
| 2006/0228316 A1* | 10/2006 | Cannell | A61K 8/19 424/70.2 |
| 2007/0041921 A1* | 2/2007 | Neill | A61K 8/19 424/70.2 |
| 2007/0067924 A1 | 3/2007 | Beck | |
| 2007/0264208 A1 | 11/2007 | Mougin | |
| 2008/0066773 A1 | 3/2008 | Anderson et al. | |
| 2008/0138309 A1 | 6/2008 | Malle et al. | |
| 2008/0141468 A1 | 6/2008 | Cotteret | |
| 2008/0187506 A1 | 8/2008 | Carballada et al. | |
| 2009/0022681 A1 | 1/2009 | Carballada et al. | |
| 2009/0126756 A1 | 5/2009 | Syed et al. | |
| 2009/0252697 A1 | 10/2009 | Barbarat | |
| 2010/0004391 A1 | 1/2010 | Huddleton et al. | |
| 2010/0202998 A1 | 8/2010 | Ramos-Stanbury et al. | |
| 2011/0256084 A1 | 10/2011 | Dixon et al. | |
| 2012/0180807 A1 | 7/2012 | Flohr | |
| 2012/0244082 A1 | 9/2012 | Sulzbach | |
| 2013/0152959 A1 | 6/2013 | Genain | |
| 2013/0172518 A1 | 7/2013 | Huang et al. | |
| 2013/0309190 A1 | 11/2013 | Dimotakis et al. | |
| 2014/0186283 A1 | 7/2014 | Cabourg | |
| 2014/0196741 A1 | 7/2014 | Cabourg | |
| 2015/0034117 A1 | 2/2015 | Pressly | |
| 2015/0034119 A1 | 2/2015 | Pressly | |
| 2015/0297496 A1 | 10/2015 | Kroon | |
| 2016/0081899 A1 | 3/2016 | Pressly | |

FOREIGN PATENT DOCUMENTS

| | | |
|---|---|---|
| DE | 100 51 773 | 4/2002 |
| DE | 100 51 774 | 4/2002 |
| DE | 10051773 | 4/2002 |
| DE | 10051774 | 4/2002 |
| DE | 102004052480 | 5/2006 |
| DE | 202015104742 | 10/2015 |
| EP | 0299764 | 1/1989 |
| EP | 0 298 684 | 4/1993 |
| EP | 0298684 | 4/1993 |
| EP | 0978272 | 2/2000 |
| EP | 1 174 112 | 1/2002 |
| EP | 1174112 | 1/2002 |
| EP | 2295029 | 3/2011 |
| EP | 2478892 | 7/2012 |
| FR | 2975900 | 12/2012 |
| GB | 741307 | 11/1955 |
| GB | 773 559 | 4/1957 |
| GB | 773559 | 4/1957 |
| GB | 1125794 | 8/1968 |
| JP | 2006327994 | 12/2006 |
| JP | 2009007283 | 1/2009 |
| KR | 10-2003-0003970 | 1/2003 |
| KR | 1020030003970 | 1/2003 |
| KR | 10 2006-0059564 | 6/2006 |
| KR | 10-2006-0059564 † | 6/2006 |
| KR | 1020060059564 | 6/2006 |
| WO | 93/00882 A1 † | 1/1993 |
| WO | 9300882 | 1/1993 |
| WO | WO 93/00882 | 1/1993 |
| WO | 9308787 | 5/1993 |
| WO | WO 93/08787 | 5/1993 |
| WO | 9501152 | 1/1995 |
| WO | WO 95/01152 | 1/1995 |
| WO | 0232383 | 4/2002 |
| WO | 0232386 | 4/2002 |
| WO | WO 02/32383 | 4/2002 |
| WO | WO 02/32386 | 4/2002 |
| WO | 2006011771 | 2/2006 |
| WO | 2009/024936 | 2/2009 |
| WO | 2009024936 | 2/2009 |
| WO | WO 2009/024936 | 2/2009 |
| WO | 2010049434 | 5/2010 |
| WO | 2011134785 | 11/2011 |
| WO | WO 2011/134785 | 11/2011 |
| WO | 2012084532 | 1/2012 |
| WO | 2012164064 | 1/2012 |
| WO | 2012080321 | 6/2012 |
| WO | WO 2012/080321 | 6/2012 |
| WO | WO 2012/084532 | 6/2012 |
| WO | WO 2012/164064 | 12/2012 |
| WO | 2014016407 | 1/2014 |
| WO | WO 2014/016407 | 1/2014 |
| WO | 2014/072490 † | 5/2014 |
| WO | 2014118212 | 8/2014 |
| WO | 2014125452 | 8/2014 |
| WO | WO 2014/118212 | 8/2014 |
| WO | 2014167508 | 10/2014 |
| WO | WO 2014/167508 | 10/2014 |
| WO | 2015017768 | 2/2015 |
| WO | 2015026994 | 2/2015 |
| WO | WO 2015/017768 | 2/2015 |
| WO | WO 2015/026994 | 2/2015 |
| WO | 2015175986 | 11/2015 |
| WO | WO 2015/175989 | 11/2015 |

OTHER PUBLICATIONS

Olaplax,, Apparent description of booth presentation during Bronner Bros. show in Atlanta where demonstrations we presented to show how to mix Olaplex with hydroxide relaxers, http://www.instagram.com/p/zacpQuIJfn/, Instagram post Feb. 22, 2015.

Refinery, "Fire Your Colorist if They Are Not Using This" http://www.refinery20.com/olaplex-hair-color, 6 pages, retrieved from the internet Jun. 24, 2016.

The Power of One http://www.nxtbook.com/nctbooks/creativeage/Launchpad_201405/index.php?srartid, 401 page, retrieved from the internet Jun. 24, 2016.

Third Party Observation filed in European Application No. 14758005.4 (May 13, 2016).

Third Party Observation filed in European Application No. 14758005.4 (May 18, 2016).

Third-Party observations for GB1513932.2 (Jun. 24, 2016).

Written Opinion for PCT/US2016/031166 mailed Jul. 19, 2016.

Zviak, The science of hair care, Marcel Dekker, Inc., pp. 263-279 (1986).

Dombrink and Tanis, "pH & hair shampoo", *Chem Matters*, p. 8 (1983).

Hall and Wolfram, "Application of the theory of hydrophobic bonds to hair treatments", *J Soc Cosmet Chem.*, 28:231-41 (1977).

Koval, "Reactions of Thiols", *Russian J Organic Chemistry*, 43(3):319-49 (2007).

Majonis, et al., "Dual-purpose polymer labels for fluorescent and mass cytometric affinity bioassays", *Biomacromolecules*, 14(5):1503-13 (2013).

Mintel Leave-in Hair and Scalp Nutrient, XP002743522, Database accession No. 10141004, Jun. 1, 2003.

Mintel Permanent Hair Colour, XP002743523, Database Accession No. 2061070, May 1, 2013.

Mintel Database, Record ID 743214, Catzy Hair Colourant, 4 pages, Published Jul. 2007.

Salvin, et al. "Biological surface modification by 'thiol-ene' addition of polymers synthesized by catalytic chain transfer polymerization (CCTP)", Polymer Chem., 3:1461-6 (2012).

Shansky, "The Reaction Mechanism of Fiber Reactive Dyestuffs with Hair Keratin", American Perfumer and Cosmetics, 81:23-27 (1966).

Shansky, "Toning of Human Hair with Fiber Reactive Dyestuffs", Cosmetics and Toiletries, 91(11):46-48 (1976).

Thermo FisherScientific, "Bismaleimide Crosslinkers (BMOE, BMB and BMH)", product instructions, pp. 1-3 (2012).

Yan, et al., "Cellular association and cargo release of redox-responsive polymer capsules mediated by exofacial thiols", *Adv Mater.*, 23:3916-21 (2011).

(56) References Cited

OTHER PUBLICATIONS

International Search Report for PCT application No. PCT/US2014/049388 mailed Oct. 29, 2014.
Partial International Search Report for PCT application PCT/US2015/031166 mailed Sep. 14, 2015.
Combined Search and Examination Report mailed Sep. 14, 2015 in connection with UK patent application No. GB1513932.2.
Third-Party Observations Submitted in GB 1513932.2 (Jan. 2016).
WPI Abstract Accession No. 1995-355152, English Abstract of JPH 07242520, Sep. 19, 1995, retrieved Feb. 2, 2016.
Combined Search and Examination Report for GB 1523109 mailed Feb. 4, 2016.
International Search Report for PCT application, PCT/US2015/031166, mailed Jan. 22, 2016.
Official Communication in UK Patent Application No. 1513932.2 (Apr. 13, 2016).
Third-Party Observations Submitted in UK Patent Application No. 1513932.2 (Apr. 20, 2016).
Partial International Search Report for PCT application, PCT/US2015/065032, mailed May 9, 2016.
Combined Search and Examination Report mailed Sep. 14, 2015 in connection with UK patent application, GB1513932.2.
Dombrink and Tanis "pH & hair shampoo", Chem Matters, p. 8 (1983).
Hall and Wolfram, "Application of the theory of hydrophobic bonds to hair treatments", J Soc Cosmet Chem., 28:231-41 (1977).
International Search Report and Written Opinion for PCT/US2014/049388 mailed Oct. 29, 2014.
International Search Report for PCT/US2015/031166, mailed Jan. 22, 2016.
Koval, "Reactions of Thiols", Russian J Organic Chemistry, 43(3):319-49 (2007).
Partial International Search Report for PCT application PCT/US2015/031166 mailed Sep. 14, 2015.
Salvin, et al. "Biological surface modification by thiol-enel addition of polymers synthesized by catalytic chain transfer polymerization (CCTP)", Polymer Chem., 3:1461-6 (2012).
Shansky, "The Reaction Mechanism of Fiber Reactive Dyestuffs with Hair Keratin", American Perfumer and Cosmetics (1966).
Shansky, "Toning of Human Hair with Fiber Reactive Dyestuffs", Cosmetics and Toiletries (1976).
Thermo FisherScientific, "Bismaleimide Crosslinkers (BMOE, BMB and BMH)", product instructions, pp. 1-3 (2012).
Third-Party Observations Submitted in UK 1513932.2 (Apr. 20, 2016).
Third part observation for GB 1513932.2 (Jan. 2016).
Yan, et al., "Cellular association and cargo release of redox-responsive polymer capsules mediated by exofacial thiols", Adv. Mater., 2011, 23, 3916-3921.
Facebook page, https://www.facebook.com/behindthechair/photos/a.153398501906.116563.44389181906/10152417864161907/?type=3&theater ; May 13, 2014.
Facebook page, https://www.facebook.com/GuyTangHairArtist/photos/a.254923251198058.69129.214382105252173/762062380484140/?type=3&theater; Apr. 17, 2014a.
Facebook page, https://www.facebook.com/GuyTangHairArtist/photos/a.254923251198058.69129.214382105252173/762551773768534/?type=3&theater ; Apr. 17, 2014b.
Facebook page, https://www.facebook.com/GuyTangHairArtist/photos/a.254923251198058.69129.214382105252173/767530266604018/?type=3&theater ; Apr. 26, 2014.
Facebook page, https://www.facebook.com/GuyTangHairArtist/photos/a.254923251198058.69129.214382105252173/772484942775217/?type=3&theater; May 7, 2014.
Facebook page, https://www.facebook.com/olaplex/573114059463275; Apr. 7, 2014.
Facebook page, https://www.facebook.com/olaplex/photos/a.541423639298984.1073741828.347578558683494/574713415970006/?type=3&theater; Apr. 11, 2014.
Facebook page, https://www.facebook.com/traceycunninghamcolor/posts/10152466366701095; May 11, 2014.
Facebook page, https://www.facebook.com/traceycunninghamcolor/posts/10202245158143314; Mar. 9, 2014.
Guy Tang on Instagram page, https://www.instagram.com/p/nPmHn7mnA6/; Apr. 26, 2014.
Olaplex on Instagram page, https://www.instagram.com/p/mGhswioJQ2/?hl=en; Mar. 28, 2014.
Olaplex on Instagram page, https://www.instagram.com/p/mvxsbUoJSI/?hl=en; Apr. 13, 2014.
Olaplex on Instragram page, https://www.instagram.com/p/nBwLbtoJck/?hl=en; Apr. 20, 2014.
Tracey Cunningham on Instagram page, https://www.instagram.com/p/l_mat6ig-z/; Mar. 26, 2014.
Tracey Cunningham on Instagram page, https://www.instagram.com/p/I1AF_Zig5e/; Mar. 22, 2014.
"Relaxing agents," Milday Standard Cosmetology, pp. 618-625, 13th edition, (2016).
Ramachandra, et al., "Acid-based characteristics of human hair: Absorption of HCl and NaOH, and the effects on physical properties." J Soc Comet Chem., 32:393-405 (1981).

\* cited by examiner
† cited by third party

METHODS FOR TREATING RELAXED HAIR

CROSS-REFERENCE TO RELATED APPLICATION

This application claims benefit of and priority to U.S. Provisional Application No. 62/152,220, filed Apr. 24, 2015, which is incorporated herein by reference in its entirety.

FIELD OF THE INVENTION

The present invention generally relates to compositions and methods for treating hair, particularly for repairing disulfide bonds in hair treated with a lye or alkali-based relaxer and for controlling the level of curl retention in the relaxed hair.

BACKGROUND OF THE INVENTION

Hair consists of many long, parallel chains of amino acids. These chains, or polymers, of amino acids are bound to each other via 1) hydrogen bonding, 2) salt bridges between acid and base groups, and 3) disulfide bonds.

At alkaline pH, the disulfide bonds in hair can be broken (Dombrink et al., *Chem Matters*, 1983, page 8). For example, lye-based relaxers contain hydroxide ions which attack the disulfide linkages. The disruption of disulfide bonds by the lye-based relaxer is used to achieve straightening of the hair through changing of the relative positions of opposing polypeptide chains. The straightening process is completed by rinsing the hair and/or application of a neutralizing composition.

While lye and other alkali-based relaxers are highly effective at relaxing and straightening hair they can result in reduction of hair strength and potential loss of hair through breakage. Relaxing hair can therefore be viewed as a destructive and irritating process which can strip hair of its natural fatty acids. Exposing hair to alkaline conditions also damages the hair and further causes the cuticle or outer surface of the hair strands to become roughened and can result in ruffled, tangled, and generally unmanageable hair. Roughened hair catches light unevenly and makes the hair look lusterless and dull. The hair can also be left with increased levels of static upon drying, which can interfere with combing and result in a condition commonly referred to as "fly-away hair."

A variety of approaches have been developed to alleviate these problems, including post-shampoo application of hair conditioners, such as leave-on and rinse-off products. Typically, conditioning rinses put back the oily coating, especially to the damaged portion of the hair where the cuticle has become ruffled since conditioners cling best to these portions. However, too much or too heavy a conditioner will make the hair stickier, thus attracting dirt and often may make more shampooing treatments necessary.

Yet another issue with the use of lye and other alkali-based hair relaxers is that their application leads to completely relaxed and straightened hair without any level of curl and/or any controllably retained level of curl. Furthermore, due to the reduction of hair strength and potential loss of hair due to breakage from such relaxing processes, any further application of a permanent wave process (i.e., to introduce a controlled amount of curl) to the already relaxed and straightened hair would be inadvisable as it would result in further damage and/or breakage of the hair.

Thus, there is a need for hair formulations and treatments that can provide improved conditioning benefit for hair relaxed with lye or alkali-based relaxers. Specifically, there is a need to provide long lasting moisturized feel, smooth feel, and manageability control to the treated hair when it is dried.

There is also a need for hair formulations and treatments that repair and/or strengthen damaged hair treated with lye or alkali-based relaxing agents or hydroxide-containing relaxing agents.

There is also a need for hair formulations and treatments that afford the ability to tune or select the level of curl achieved and/or retained in hair which has been relaxed with lye or alkali-based relaxing agents or hydroxide-containing relaxing agents.

Therefore, it is an object of this invention to provide improved compositions and methods for repairing and/or strengthening hair treated with lye or alkali-based relaxing agents or hydroxide-containing relaxing agents.

It is a further object of this invention to provide compositions and methods which can be used to tune or select the level of curl achieved and/or retained in hair that has been treated with lye or alkali-based relaxing agents or hydroxide-containing relaxing agents.

SUMMARY OF THE INVENTION

Compositions, kits, and methods for repairing bonds, for example, disulfide bonds, in relaxed hair that has been damaged by treatment with a lye or alkali-based relaxing agent(s) or hydroxide-containing relaxing agents. The compositions, kits, and methods can also be used to control the level of curl retention during the relaxing process.

Active agent formulations, which contain one or more compounds that interact with keratin through one or more binding events (e.g., absorption, binding, etc.) which may involve reaction with one or more thiols in the hair are described herein. "Binding" as used herein refers to the formation of covalent, ionic, or hydrogen bonds. The active agent compositions can provide improved conditioning and provide long lasting moisturized feel and smooth feel without leaving the hair greasy, improve appearance (e.g., sheen), increase dry strength (tensile strength), ease combing of the hair when wet or dried, reduce hair breakage, or decrease frizz, or any combination thereof.

Without being bound by theory, it is believed that use of the active agent formulations prevents reversion of the hair's repaired bonds to their free thiol state, for at least one week, two weeks, three weeks, four weeks, one month, or two months, or longer, after application of the composition.

Traditional methods of straightening hair make use of lye or alkali-based relaxers or hydroxide-containing relaxing agents which can result in reduction of hair strength and potential loss of hair through breakage. The methods disclosed herein use active agents which can repair damage to relaxed hair and also provide improved methods of styling hair, such as during a hair relaxing/straightening treatment using lye or alkali-based relaxers or hydroxide-containing relaxing agents.

The active agent formulations can be applied during the hair relaxing treatment along with the relaxing agent. Without wishing to be bound by any particular theory, the addition of the active agents described herein simultaneously with a lye or alkali-based relaxing agent or hydroxide-containing relaxing agent can be used to tune or control the level of curl retention in the relaxed hair. The level of curl retention can depend on the amount of active agent(s) used, which can be represented as a weight ratio of active agent present in the hair relaxing to the amount of lye or alkali-based relaxing agent present. Typically, the greater the amount of active agent present in the relaxing formulation the greater the level of curl retention. In some embodiments, the weight ratio of the relaxing agent formulation to the active agent formulation is in the range of about 1:10 to about 10:1. The inclusion of the one or more active agents permits not only control of the level of curl retention during hair relaxation but further allows for repair of the disulfide bonds broken during the relaxation process to otherwise prevent damage caused by the relaxing agent(s).

In some other embodiments, the active agent formulations can be applied immediately following the application of the lye or alkali-based relaxing agent(s) or hydroxide-containing relaxing agents.

DETAILED DESCRIPTION OF THE INVENTION

I. Definitions

Numerical ranges disclosed herein disclose individually each possible number in such range, as well as any sub-ranges and combinations of sub-ranges encompassed therein. For example, a carbon range (i.e., $C_1$-$C_{10}$) is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed within, such as $C_2$-$C_9$, $C_3$-$C_8$, $C_1$-$C_5$, etc. Similarly, an integer value range of 1-10 discloses the individual values of 1, 2, 3, 4, 5, 6, 7, 8, and 10, as well as sub-ranges encompassed within. Further, a concentration range or weight percent range, such as from 1% to 2% by weight of the formulation discloses, the individual values and fractions thereof, such as 1%, 1.1%, 1.2%, 1.32%, 1.48% etc., as well as sub-ranges encompassed within.

The term "hair" refers to one or more than one strand of hair, as well as the natural components of hair, such as oil from a body. Hair also refers to virgin hair or processed hair, for example hair that has been exposed to hair waving or hair straightening formulations.

An "effective amount", e.g., of the active agent or compositions described herein, refers to an amount of the active agent in a composition or formulation which, when applied as part of a desired hair treatment achieves the desired result, such as curl retention, smoothness, little or no breakage, great or good feel, and/or healthy appearance by visual inspection.

"Cosmetically acceptable" refers to those compounds, materials, and compositions, which are, within the scope of sound medical judgment, suitable for use in contact with the tissues of human beings and animals without excessive toxicity, irritation, allergic response, or other problems or complications commensurate with a reasonable benefit/risk ratio. More specifically, cosmetically acceptable refers to a material, compound, or composition which is suitable for use in contact with the skin, scalp, or hair. Cosmetically acceptable materials are known to those of ordinary skill in the art.

"Shampoo", as used herein, generally refers to a liquid or semi-solid formulation applied to the hair that contains detergent or soap for washing the hair.

"Conditioner", as used herein, generally refers to a formulation (e.g., liquid, cream, lotion, gel, semi-solid) applied to the hair to soften the hair, smooth the hair, and/or change the sheen of the hair.

"Analog" and "Derivative" are used herein interchangeably and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Electrophilic group" or "electrophilic moiety" are used interchangeably and refer to one or more functional groups or moieties that have an affinity for or attract electrons.

"Michael acceptor", as used herein, is a species of electrophilic groups or moieties that participates in nucleophilic addition reactions. The Michael acceptor can be or can contain an $\alpha,\beta$-unsaturated carbonyl-containing group or moiety, such as a ketone. Other Michael acceptors include pi-bonds, such as double or triple bonds conjugated to other pi-bond containing electron withdrawing groups, such as nitro groups, nitrile groups, and carboxylic acid groups.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms, such as nitrogen, may have hydrogen substituents and/or any permissible substituents of organic compounds described herein that satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Polymer", as used herein, refers to a molecule containing more than 10 monomer units.

"Water-soluble", as used herein, generally means at least 50, 75, 100, 125, 150, 200, 225, or 250 g is soluble in 1 L of water at 25° C.

"Relaxing agents," as used herein typically refers to hydroxide-containing compounds, such as lye or other hydroxide-containing compounds, such as ammonium hydroxide. When these hydroxide-containing compounds are present in a hair relaxing formulation the hydroxide ions produce a relaxing formulation with a high pH.

"Lye," or "lye relaxer," are used interchangeably herein and refer to an aqueous formulation or composition containing an alkali metal containing hydroxides (e.g. Sodium hydroxide and/or Potassium hydroxide).

II. Active Agent Formulations

The active agent formulations disclosed herein are concerned with treating hair which is either in the process of being relaxed or has undergone a relaxing treatment with a relaxing agent containing formulation. Additionally, the active agent formulations, when used during the relaxing treatment can be used to control, select, or tune the level of curl achieved and/or retained in the relaxed hair, as compared to the hair's natural unrelaxed state. The level of curl retention depends on the amount of one or more active agents applied, which can be represented as a weight ratio of the weight of one or more active agents (or the weight of the active agent containing formulation) to the weight of the hair relaxing formulation. Typically, the greater the amount of active agent present in the relaxing formulation the greater the level of curl retention which can be achieved. Furthermore, the inclusion of one or more active agents, as described herein, permits control of the level of curl retention during hair relaxation while reducing hair breakage and damage during the relaxation process caused by the relaxing agent(s).

The formulations contain one or more active agents (also referred to herein as "compounds" or "active agents") which can be combined with one or more cosmetically acceptable carriers and/or excipients that are considered safe and effective to human hair and/or human scalp, and may be administered to an individual's hair without causing undesirable biological side effects, such as burning, itching, and/or redness, or similar adverse reactions.

The active agent is typically present in an amount ranging from about 0.01 wt % to about 50 wt % of the formulation, preferably from about from about 1 wt % to about 25 wt % of the formulation, more preferably from about 1 wt % to about 15 wt %, most preferably from about 1 wt % to about 10 wt %. Typically, the active agent may be present in an amount ranging from about 1 to about 5 wt % of the formulation.

The active agent is stable in aqueous solution for a period of at least 2, 3, 4, 5, 6, 8, 9, 10, 11, or 12 months or longer at pH of 3 to 8, preferably 3 to 5, and a temperature of about 25-30° C., preferably about 25° C. "Stable" as used herein with respect to shelf-life means that at least 40, 45, 50, 55, 60, 65, 70, 75, 80, 85, 90, or 95% of the compound is unchanged over the specified time period.

a. Active Agent

The active agent contains at least one reactive moiety capable of reacting with and forming bonds with a nucleophile, such as a thiol. The active agents optionally contain a linker group. The reactive moieties, upon reaction with thiol groups on the hair follicle, form bonds that are stable, for example, hydrolytically stable. "Stable", as used in reference to the bonds formed between thiol groups on hair follicles means the bonds remain intact for at least one week, two weeks, three weeks, four weeks, one month, or two months or longer when exposed to water at a pH of 3 to 8, preferably at a pH of 3 to 5, at a temperature from about 5° C. to about 100° C., from about 20° C. to about 75° C., more preferably from about 20° C. to about 50° C., from about 25° C. to about 40° C., or from about 25° C. to about 30° C., and more preferably at a temperature of about 25° C. In some embodiments, the temperature is about 25° C. It is also preferred that the reaction between the reactive moieties and thiol occur around room temperature, for example, from about 15° C. to about 35° C., preferably from about 20° C. to about 30° C., more preferably from about 22° C. to about 27° C.

i. Active Agents Defined by Formula I

In some embodiments, the binding agents have a structure according to Formula I:

Formula I wherein

A, B, C, and D are reactive moieties containing one or more charges,

R is a linker that contains two or more charges, wherein the charges are opposite to the charges on the reactive moieties, wherein n=1-100, preferably n=1-10, more preferably n=1; and each occurrence of p, q, r, and s is independently an integer from 0 to 25, preferably from 0 to 10, more preferably from 0 to 2. The sum of p+q+r+s is equal to or greater than 2.

The reactive moieties may be present on any atom of the linker. In some embodiments, the reactive moieties are the same. In some embodiments, one or more of the reactive moieties is different.

In some embodiments, the reactive moieties are negatively charged and the linker or spacer has positively charged moieties. In other embodiments, the reactive moieties are positively charged and the linker or spacer has negatively charged moieties. Generally, the sum of the charges on the binding agent of Formula I is zero though stoichiometric imbalances may exist.

The reactive moieties on the binding agents are preferably linked via a linker R. The linker R, as used herein, refers to one or more polyfunctional, e.g. bifunctional molecules, trifunctional molecules, tetrafunctional molecules, etc., which can be used to ionically bound the two or more reactive moieties and which do not interfere with the reactive properties of the binding agents. The reactive moieties may be attached to any part of linker R.

1. Linker R

In a preferred embodiment, in Formula I, n=1 and the linker R is not a polymer. The linker R can be a single atom, such as a heteroatom (e.g., O or S), a group of atoms, such as a functional group (e.g., amine, —C(=O)—, —CH$_2$—), or multiple groups of atoms, such as an alkylene chain. Suitable linkers include but are not limited to oxygen, sulfur, carbon, boron, nitrogen, alkoxy, alkyl, alkenyl, cycloalkyl, cycloalkenyl, aryl, heterocycloalkyl, heteroaryl, ether, amine, and a polymer.

The linker R is optionally independently substituted with one or more substituents including hydrogen, halogen, cyano, alkoxy, alkyl, alkenyl, cycloalkyl, cycloalkenyl, aryl, heterocycloalkyl, heteroaryl, amine, hydroxy, formyl, acyl, carboxylic acid (—COOH), —C(O)R$^1$, —C(O)OR$^1$, carboxylate (—COO$^-$), primary amide (e.g., —CONH$_2$), secondary amide (e.g., —CONHR$^1$), —C(O)NR$^1$R$^2$, —NR$^1$R$^2$, —NR$^1$S(O)$_2$R$_2$, —NR$^1$C(O)R$^2$, —S(O)$_2$R$^2$, SR$^1$, and —S(O)$_2$NR$^1$R$^2$, sulfinyl group (e.g., —SOR$^1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or =O or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In some embodiments, the linker R may be an alkoxy, ether, alkyl, alkenyl, cycloalkyl, cycloalkenyl, aryl, heterocycloalkyl, heteroaryl, amine, or a polymer.

2. Active Agents According to Formula I

The active agent according to Formula I contains at least two reactive moieties that are capable of reacting with thiols or amines to form covalent bonds. For example, the reactive moieties are capable of reacting with a thiol group in the hair to form a stable covalent bond. The reactive moiety is typically an electrophilic moiety capable of forming a salt with the linker. Alternately, the reactive moiety can be capable of reacting with a free radical.

The active agent according to Formula I contains at least two reactive moieties. However, the binding agent may contain three, four, five, six, or greater than six reactive moieties.

The reaction between the reactive moiety and the thiol groups may be initiated at room temperature and pressure when the reactive moiety contacts a thiol group in the hair. In some embodiments, the reaction may require an initiator, such as heat, catalyst, basic conditions, or a free radical initiator. The rate of reaction between the reactive moiety and the thiol may be increased by changes in temperature, pH, and/or addition of one or more excipients, such as a catalyst; however, this is generally not required.

The two or more reactive moieties on the binding agent can be the same. In some embodiments, the two or more reactive moieties are different.

In some embodiments, the reactive moieties are capable of undergoing a conjugate additional reaction. The reactive moieties can independently be or contain a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

In the preferred embodiments, each of reactive moieties A, B, C, and/or D when present independently contains a moiety selected from the group consisting of a vinyl sulfone, an acrylate group, a methacrylate group, a styrene group, an acryl amide group, a methacryl amide group, a maleate group, a fumarate group, and an itaconate group. Further, in the preferred embodiments, n=1 and the linker R is not a polymer. Optionally, all of the reactive moieties are the same. For example, in some embodiments all of the reactive moieties are maleate groups.

In some embodiments, the active agent according to Formula I has one of the following structures:

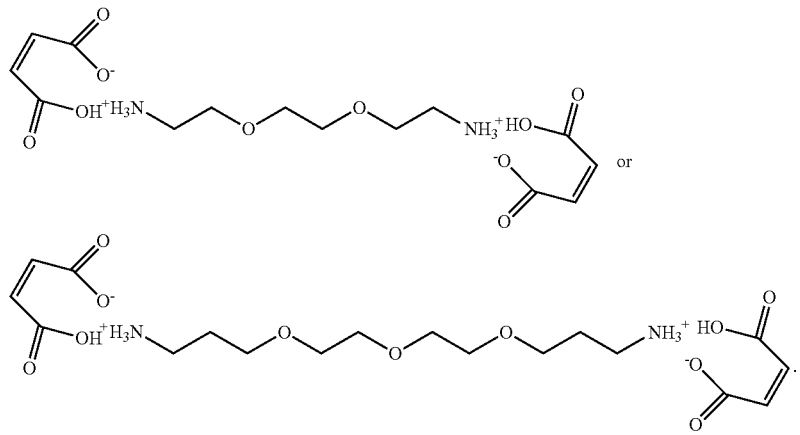

Active agents according to Formula I are further described in U.S. Patent Publication No. 2015/0034117 A1 to Pressly, et al. and issued as U.S. Pat. No. 9,095,518, which is incorporated herein by reference with respect to its disclosure of active agents.

ii. Active Agents Defined by Formula II

In some other embodiments, the active agent is a polyfunctional compound that contains ionizable functional groups capable of forming ionic bonds and functional groups capable of forming a covalent bond with a nucleophile, such as a thiol or an amine. Suitable ionizable functional groups include, but are not limited to, acidic groups such as carboxylic acids, sulfonic acids, phosphonic acids, and basic groups, such as amines. Suitable functional groups capable of forming a covalent bond with a nucleophile, such as a thiol or an amine, include, but are not limited to, Michael acceptors, alkyl halides or sulfonate esters.

The active agent may have the following Formula II:

(B)$_m$—Z-(A)$_n$    Formula II wherein Z is a linker or is absent, m and n are each an integer independently selected from 1-6, provided that m+n is at least 2, B is a functional group capable of forming a covalent bond with a thiol or amine group, and A is an ionizable functional group. Preferably, the linker Z is not a polymer.

Exemplary active agents according to Formula II may contain thiol reactive functional groups, as group B, for example, such as those shown in the following moieties:

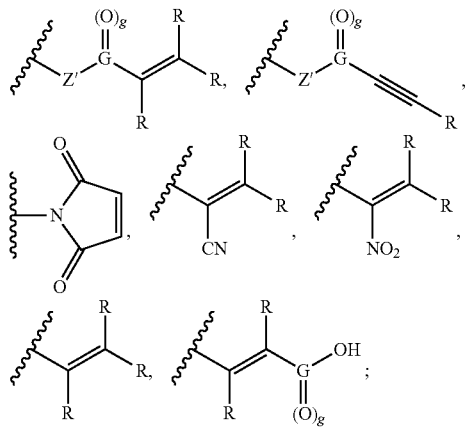

wherein R is independently selected from hydrogen, C$_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

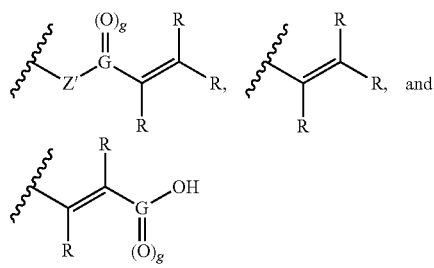

wherein R, Z', G, and g are as previously defined.

1. Linker Z

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$_{11}$), —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$_1$), and sulfonyl group (e.g., —SOOR$_1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a C$_{1-10}$ alkyl group which may be unsubstituted or substituted one or more times by oxo, hydroxyl, carboxyl, amido or amino. Preferably, the linker Z is a C$_{1-4}$ alkyl group. The alkyl group may be linear or branched. The alkyl group may also be interrupted one or more times by a heteroatom selected from oxygen, sulfur and nitrogen. An example of such a di-carboxylic acids having a heteroatom interruption is thiodi-propionic acid. In other embodiments, the alkyl group may contain one or more double or triple bonds.

In some embodiments, the active agent according to Formula II has one of the following structures:

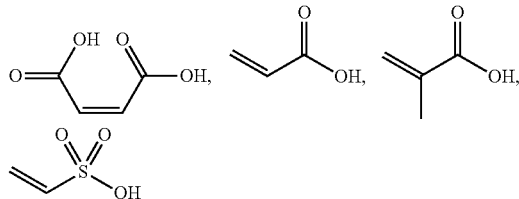

or is a simple salt of these structures.

iii. Active Agents Defined by Formula III

In certain other embodiments, the active agent may have the following Formula III:

$$(B)_m\text{—}Z\text{-}(A)_n\text{-}(C)_o \qquad \text{Formula III}$$

wherein Z is a linker or is absent, m and n are each an integer independently selected from 1-6, provided that m+n is at least 2, B is a functional group capable of forming a covalent bond with a nucleophile, such as a thiol or amine group, A is an ionizable functional group as defined above, and C is an ionic group which is also capable of forming a covalent bond with a thiol and which has a charge opposite to that of ionizable group A. Group C is ionically bonded (denoted by dashed line) to group A. For ionic group C, o is an integer value independently selected from 1-6, such that the sum of charges of group C and ionizable group A is zero. Preferably linker Z is not a polymer.

In active agents of Formula III, group C is an ionic group which is ionically bonded to ionizable group A and contains at least one thiol reactive. Group C may be a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

The active agents according to Formula III may contain thiol reactive functional groups which react with a nucleophile, such as a thiol, as group B. Examplary thiol reactive functional groups include, but are not limited to, those shown in the following moieties:

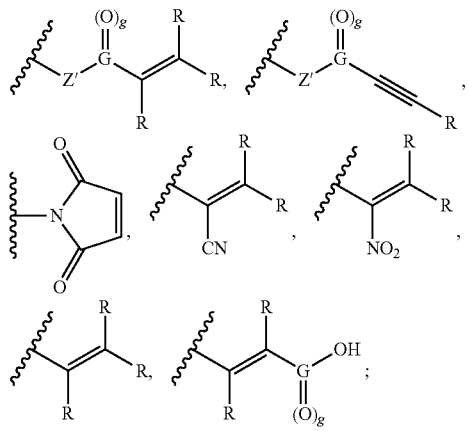

wherein R is independently selected from hydrogen, $C_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

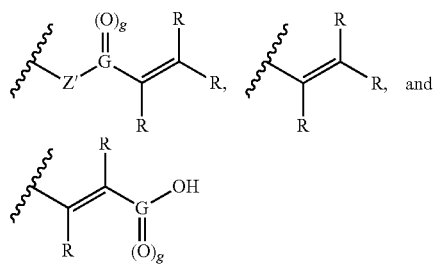

wherein R, Z', G, and g are as previously defined.

1. Linker Z

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$_{11}$), —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$_1$), and sulfonyl group (e.g., —SOOR$_1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a $C_{1-10}$ alkyl group which may be unsubstituted or substituted one or more times by oxo, hydroxyl, carboxyl, amido or amino. Preferably, the linker Z is a $C_{1-4}$ alkyl group. The alkyl group may be linear or branched. The alkyl group may also be interrupted one or more times by a heteroatom selected from oxygen, sulfur and nitrogen. An example of such a dicarboxylic acids having a heteroatom interruption is thiodipropionic acid. In other embodiments, the alkyl group may contain one or more double or triple bonds.

In some embodiments, the active agent of Formula III has one of the following structures:

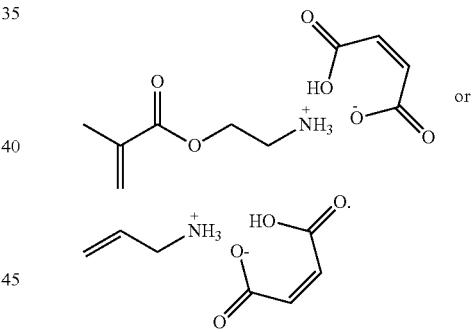

b. Excipients

The active agent formulations can typically contain one or more cosmetically acceptable excipients. Cosmetically acceptable excipients include, but are not limited to, water, preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

The formulations may contain one or more cosmetically acceptable excipients. In some forms, the formulations contain the active agent, water, and optionally a preservative and/or fragrance.

The formulation for treating hair during or immediately following a relaxation process with a relaxing formulation may be in any suitable physical form. Suitable forms include, but are not limited to low to moderate viscosity liquids, lotions, milks, mousses, sprays, gels, creams, shampoos, conditioners, and the like. Suitable excipients, such as those listed above, are included or excluded from the hair care formulation depending on the form of use of the formulation (e.g., hair spray, cream, conditioner, or shampoo).

The cosmetically acceptable excipient is typically present in an amount ranging from about 10 wt % to about 99.99 wt % of the formulation, preferably about 40 wt % to about 99 wt %, more preferably from about 80 wt % to about to about 99 wt %.

i. Surfactants

Surfactants are surface-active agents that are able to reduce the surface tension of water and cause the formulation to slip across or onto the hair. Surfactants may also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium $C_{12-15}$ alkyl sulfate, ammonium $C_{12-15}$ pareth sulfate, ammonium $C_{12-16}$ alkyl sulfate, ammonium $C_{9-10}$ perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine.

Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.1% to about 15% by weight of the formulation, preferably about 1% to about 10% by weight of the formulation.

ii. Emollients

Emollient refers to a material that protects against wetness or irritation, softens, soothes, coats, lubricates, moisturizes, protects, and/or cleanses the skin. Suitable emollients for use in the formulations include, but are not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or a combination thereof. More than one emollient may be included in the formulation.

The emollient is optionally included in an amount ranging from about 0.5% to about 15% by weight of the formulation, preferably from about 1% to about 10% by weight of the formulation.

iii. Emulsifiers

The formulations may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, or polysorbate-80, or combinations thereof. More than one emulsifier may be included in the formulation.

The emulsifier is optionally included in an amount ranging from about 0.05% to about 15% by weight of the formulation, preferably from about 0.1% to about 10% by weight of the formulation.

iv. Preservatives

One or more preservatives may be included in the formulations to prevent microbial growth in the formulations. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.1% to about 5% by weight of the formulation, preferably from about 0.3% to about 3% by weight of the formulation. Preferably, the formulations are paraben free.

v. Conditioning Agents

One or more conditioning agents may be included in the formulations. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) is optionally included in an amount ranging from about 0.1% to about 5% by weight of the formulation, preferably from about 0.3% to about 3% by weight of the formulation.

vi. Diluents

Diluent, as used herein, refers to a substance(s) that dilutes the active agent. Water is the preferred diluent. The formulations typically contains greater than one percent (wt) water, preferably greater than five percent (wt) water, more preferably greater than 50% (wt) water, and most preferably greater than 80% (wt) water. Alcohols, such as ethyl alcohol and isopropyl alcohol, may be used at low concentrations (about 0.5% by weight of the formulation) to enhance hair or skin penetration and/or reduce odor.

vii. Viscosity Modifying Agents

The formulations may contain one or more viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

viii. Antioxidants

The formulations may contain one or more antioxidants. Examples include, but are not limited to, tocopheryls, BHT, ascorbic acid, camellia sinensis leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

ix. Opacifying Agents

The formulations may contain one or more opacifying agents. Opacifying agents are added to the formulations to make them opaque. Suitable opacifying agents include, but are not limited to, glycol distearate and ethoxylated fatty alcohols.

c. Forms of the Formulation i. Creams

The formulation may be in the form of a cream. The cream typically includes the active agent in a suitable carrier. The active agent may be included in any suitable concentration. Typical concentrations of the active agent in the cream range from small amounts such as approximately 0.01% (wt), preferably at least 0.1% (wt), to large amounts, such as up to 50% (wt). Preferably the cream contains the active agent in a concentration ranging from 0.1% (wt) to 5% (wt), more preferably from 0.1% wt to 3% (wt). While greater concentrations of active agent could be present in the cream, they are generally not needed to achieve the desired results.

Additionally, the cream may include an oil, a hair conditioning agent, and/or a thickening agent. The cream may also include a fragrance, a plant extract, and/or a surfactant. The cream may be packaged in a tube, tub, bottle, or other suitable container.

ii. Liquid Active Agent Formulations

In some embodiments, a liquid active agent formulation is provided, which is mixed at the time of use with a second formulation, such as for relaxing hair. In these embodiments, the liquid active agent formulation may contain any suitable concentration of active agent in a suitable carrier, typically a diluent, such as described above. The concentration of the active agent is suitable to provide a mixture with the appropriate final volume and final concentration of active agent, as desired.

For example, a liquid active agent formulation can contain a concentration of active agent ranging from about 5% (wt) to about 50% (wt) or greater. In a preferred embodiment, the liquid active agent formulation contains about 5% (wt) to 20% (wt) active agent.

For straightening applications, prior to use, a sufficient volume of a liquid active agent formulation is mixed with a sufficient volume of a relaxing agent-containing formulation to form a relaxing/straightening mixture having the desired concentration of active agent. Typical concentrations of the active agent in the relaxing mixture can range from small amounts, such as approximately at least 0.01% (wt), preferably at least 0.1% (wt), to large amounts, such as up to 50% (wt). Preferably the relaxing mixture contains the active agent in a concentration ranging from 0.1% (wt) to 5% (wt), more preferably from 1% wt to 5% (wt).

III. Relaxing Formulations

A relaxing formulation contains one or more relaxing agents for straightening hair. Without being bound by theory, it is believed that the hydroxide ions in the relaxing agents attack disulfide linkages in hair and producing reduced thiol groups. The disruption of disulfide bonds by the relaxing agents is used to achieve straightening of the hair through changing of the relative positions of opposing polypeptide chains. Relaxing agent formulations and their methods of preparation are known in the art.

Exemplary relaxing agents include lye, alkali-based, or hydroxide-containing agents which include, but are not limited, to alkali metal hydroxides such as sodium hydroxide, lithium hydroxide, and potassium hydroxide. In some other embodiments, the relaxing agent is ammonium hydroxide. Hydroxide-containing relaxing agents are known to those of skill in the art. Hydroxide-containing relaxers are commercially available, such as from the following commercial brands: Mizani® Rhelaxer, Design Essentials®, and Dudley's Q®.

IV. Kits

Kits for relaxing hair or treating relaxed hair typically contain an active agent formulation containing an effective amount of an active agent.

Instructions for use of the kit are also typically provided.

The kit may further contain a formulation, also referred to herein as the relaxing formulation, capable of disrupting the disulfide bonds in the hair and producing reduced thiol groups during a relaxing process.

The relaxing agent and active agent formulations are typically provided separately and instructions are provided for simultaneously applying the relaxing agent and active agent formulations to the hair. For example, the instructions may provide for creating a mixture of the relaxing agent and active agent formulations, and then applying the mixture to the hair. Alternatively, the instructions may provide for applying the relaxing agent to the hair simultaneously while applying the active agent formulation to the hair (but not as a mixture). The instructions may also include instructions for how to select the desired amount of active agent to be used, such as by specifying a volume or mass (or range thereof) of the active agent or active agent formulation, the desired weight ratio of active agent to relaxing agent, and/or the desired weight ratio of first relaxing formulation to second active agent-containing formulation in order to control the level of curl retention in the relaxed hair.

Alternatively, instructions are provided for first applying the relaxing agent to the hair and subsequently applying the active agent formulation to the hair. The instructions may explain the amount of time (i.e., in the range of about one second to about 30 minutes, more preferably within about 60 seconds) that can pass following the application of the relaxing formulation before the application of the active agent formulation and/or the amount of active agent formulation to be applied in order to control the level of curl retention in the hair. The instructions may also include instructions for how to select the desired amount of active agent to be used, such as by specifying a volume or mass (or range thereof) of the active agent or active agent formulation, the desired weight ratio of active agent to relaxing agent, and/or the desired weight ratio of first relaxing formulation to second active agent-containing formulation in order to control the level of curl retention in the relaxed hair.

A. Relaxing Formulation

In some embodiments, the kit contains a relaxing formulation, which contains one or more relaxing agents for straightening hair as described herein. Hydroxide-containing relaxing agents are well-known to those of skill in the art.

B. Active Agent formulation

The active agent formulation contains one or more active agents as described herein. Suitable formulations containing the active agents are discussed above. The active agent formulations may be in any suitable form. Suitable forms include, but are not limited to, low to moderate viscosity liquids, lotions, gels, creams, and the like. In certain embodiments, the active agent formulation is a liquid, lotion, or cream of sufficient viscosity which can be mixed with a formulation containing one or more relaxing agents. The active agent formulation is provided in a suitable container, which depends on the form of the formulation.

In one embodiment, the active agent formulation is provided as two or more separate ingredients. For example, the active agent may be provided as a dry powder in a sealed package and the excipient provided in a vial or other container. A suitable mixing container for the active agent and the excipient may be provided.

c. Other Materials in the Kit

The kit may further contain an odor eliminator. The odor eliminator can be incorporated into the reducing formulation. Alternately, the odor eliminator is present in a suitable container for use before or after washing the active formulation from the hair. Suitable odor eliminators are known to those of ordinary skill in the art.

IV. Methods of Use

Methods for treating hair during or immediately following a relaxing process are described herein. In some embodiments, the methods include controlling, selecting, or tuning the level of curl achieved and/or retained during a hair relaxation treatment (with a relaxing formulation) by controlling the relative amount of active agent formulation to the amount of relaxing agent formulation used in a combined formulation containing both components.

In some embodiments, the method for treating hair involves applying a first formulation to the hair containing one or more relaxing agents and applying a second formulation to the hair comprising one or more active agents of Formula I, II, and/or III, as described above.

These methods produce hair with reduced damage or breakage, compared to a treatment of the hair with relaxing agent(s) alone. Further the amount of the one or more active agents of the second formulation is effective to retain a level of curl, which can be expressed as percent curl retention, in the treated hair.

A. Treatment of Hair During or Following a Hydroxide Relaxing Process

The first step in straightening hair is breaking bonds in the hair. The process for breaking the bonds results from the application of a caustic agent. The process for applying a relaxing agent in normal hair straightening procedures is known to those skilled in the art. For example, to relax or straighten hair, the hair is first washed. Second, a formulation containing one or more relaxing agents, such as a sodium hydroxide-containing solution or lotion, is applied to the hair. The hair is allowed to set for a specified period of time, and then the relaxing formulation is rinsed from the hair. Optionally, a neutralizing formulation may be applied to the relaxed hair.

In one embodiment, the active agents described herein can be applied to the hair during the relaxation process. Preferably, the active agent is applied simultaneously with the relaxing agent(s) during the straightening process. In some other embodiments, the active agent can be applied immediately following the application of the relaxing formulation, whether the relaxing formula is rinsed out or not. The active agent formulation is typically applied the same day (i.e. within 24 hours) as the relaxing formulation is applied.

a. Rinse or Wash the Hair

Optionally, the hair may be shampooed and/or conditioned prior to applying the active agent formulation. Alternately, the hair may only be neutralized and/or rinsed with water prior to application of the active agent formulation.

b. Apply the Active Agent Formulation to the Hair

The active agent formulation is applied to the hair either simultaneously during the relaxation process (i.e., in combination with the relaxing agent-containing formulation) or is applied immediately following the application of the relaxing agent formulation or, alternatively, applied at a short interval of time immediately following the application of the relaxing formulation. "Short interval," as used herein, refers to a period of time in the range of one second to 30 minutes, one minute to 20 minutes, or 5 minutes to 15 minutes. In certain other embodiments, the active agent formulation is applied within the same day following application/treatment of the hair with the relaxing formulation.

In some embodiments, a first formulation containing one or more relaxing agent(s) and a second formulation containing one or more active agent(s) are combined, mixed and applied to the hair as a single combined formulation containing both types of agents to the hair undergoing a relaxing/straightening process. In some embodiments, the weight ratio of relaxing agent(s) to active agent(s) in the combined formulation is selected to control and retain a particular level of curl, which can be expressed as percent curl retention, in the hair as compared to the hair's unrelaxed (e.g. natural) amount of curl. Typically, the lower the amount of active agent(s) relative to the amount of relaxing agents the greater the extent of straightening. Conversely, the higher the amount of active agent(s) to relaxing agent(s) present in the combined formulation the greater the level of retention of curl. Similarly, in other embodiments, the level of curl retained in the treated hair is determined by the amount of the active agent(s) present in the second formulation, where the amount of active agent(s) used is lower for a lower percentage of curl retention than the amount of active agent(s) used for a higher percentage of curl retention. Accordingly, it is possible to tune the level of curl retained in hair that is treated with lye or alkali-based relaxing agents or hydroxide-containing relaxing agents by applying a selected amount of the one or more active agent(s).

In some embodiments, the weight ratio of the first formulation containing relaxing agent(s) to the second formulation containing active agent(s) is in the range of about 1:99 to about 99:1, more preferably about 10:1 to about 1:10 and the weight ratio is effective to retain a level of the hair's unrelaxed and natural curl (i.e. before relaxing treatment). The weight ratio may be about 10:1, 9:1, 8:1, 7:1, 6:1, 5:1, 4:1, 3:1, 2:1 or 1:1 of the first formulation to the second formulation. In some preferred embodiments, the weight ratio of the first formulation to the second formulation is 8:1. In other preferred embodiments, the weight ratio of the first formulation to the second formulation is 4:1. These ratios are particularly useful with commercially available relaxing agents, such as Mizani® Rhelaxer, as shown in the Examples. The amount of the second formulation containing active agent(s) and the concentration of the active agent(s) present therein can be varied as needed when using other relaxing agents to achieve similar results. Commercially available hydroxide-based relaxer formulations typically have a pH of about 12 to 14, representing a difference in hydroxide ion concentration of about 100 times between the ends of the range. Thus, the amount of active agent(s) can be varied as a function of the pH of the relaxing formulation being used, and can be further adjusted according to the buffering capacity of each relaxer, if a buffering agent is present.

In yet other embodiments, the weight ratio of the first formulation containing relaxing agent(s) to the weight of active agent(s) is in the range of about 1:99 to about 99:1, more preferably about 10:1 to about 1:10 and the weight ratio is effective to retain a level of the hair's unrelaxed and natural curl (i.e. before relaxing treatment). In some preferred embodiments, the weight ratio of the first formulation to the weight of the active agent(s) is 40:1. In other preferred embodiments, the weight ratio of the first formulation to the weight of the active agent(s) is 20:1.

As used herein, "percent curl retention" and "percentage of curl retention" are used interchangeably to refer to the level of curl that is retained following a treatment, as compared to the hair's unrelaxed and natural amount of curl (i.e. prior to treatment with a relaxing agent). One exemplary method for determining percent curl retention of treated hair (e.g. a swatch of hair) is based on the following calculation using the formula:

$$\text{Percent Curl Retention} = (L_{ext} - L_f)/(L_{ext} - L_i) \times 100$$

where $L_{ext}$ is the length of hair prior to treatment when fully extended, $L_f$ is the final (non-extended) length of the hair following a treatment, and $L_i$ is the initial (non-extended) length of hair in its initial (i.e. unrelaxed) state with its natural amount of curl, and where $L_{ext}$ does not equal $L_i$. For example, the level of curl (percent curl retention) to be retained following treatment with the active agent(s) and relaxing agent(s) can be in the range of about 0-99%, more preferably less than about 90%, more preferably less than about 80%, more preferably less than about 70%, more preferably less than about 60%, more preferably less than about 50%. In certain embodiments, the level of curl retained is between 0% and 10%. In other embodiments, the percent curl retention is greater than 50%.

In embodiments where the hair is straightened with little to no curl remaining in the hair, the level of curl retaining is less than about 10%, such as from about 10% to 0%, from about 5% to 0%, or from about 1% to 0%.

The percent of curl retention of the hair following treatment can be maintained with no appreciable or substantially (i.e., less than about 5%, 4%, 3%, 2%, or 1%) no appreciable change in its level of curl for a period of time in the range of one week to six months, more preferably two weeks to four months, and most preferably one month to three months. In some embodiments, the percentage of curl retention can be maintained for at least about one week, two weeks, three weeks, four weeks, one month, two months, three months, four months, five months, six months, or longer.

In some embodiments, the active agent-containing second formulation is is applied to the hair immediately after the application of a first relaxing agent-containing formulation, while in other embodiments a short interval of time is permitted to pass prior to application of the active agent containing formulation (e.g. 10, 15, 25, 30, 45, or 60 seconds or longer following relaxing formulation application). The hair being treated does not have to be washed or rinsed prior to the application of the active agent containing formulation. In some embodiments, the intervening period of time between the application of the relaxing agent(s) and the subsequent application of the active agent formulation and/or the amount of active agent formulation applied to the relaxing hair can be used to control the percent curl retention in the relaxed hair. In some embodiments, the amount of time between the application of the relaxing agent containing formulation and the application of the active agent containing formulation can be selected to achieve a desired amount or range of percent curl retention.

In some embodiments, the active agent formulation may be applied in a single application, or application may be repeated one or more times as needed.

Typically, the amount of active agent formulation applied is sufficient to saturate the hair. The volume of active formulation applied to the hair in each application may be about 1 to about 100 mL per person depending on their length and volume of hair. In some embodiments, application of the active agent can be repeated immediately (e.g. within about 10 to 15 seconds) or between about one and five minutes, greater than five minutes, between about five and ten minutes, greater than ten minutes, between about ten and twenty (20) minutes after the initial application of the active agent formulation.

The active agent formulations described herein which are applied in combination with relaxing agent(s) or immediately subsequent to the application of a relaxing treatment can improve hair quality, such as appearance (e.g., sheen) and feel, increase wet and dry strength, and decrease hair breakage when the hair is subjected to subsequent treatments, such as coloring.

In some embodiments, hair breakage can be decreased by 5, 10, 15, 20, 25, 30, 35, 40, 45, 50, 55, 60, 65, 70, or 75% or higher after treatment with the active agent, as compared to relaxed hair excluding the use of an active agent formulation. Hair breakage is a significant problem encountered during typical hair relaxing treatments.

c. Remove the Relaxing and/or Active Agent Formulation from the Hair

The treated hair can be washed, rinsed, shampooed, or conditioned subsequent to the relaxing process including the application of an active agent formulation. The hair may be rinsed and subsequently washed immediately (e.g. within 10, 15, 25, 30, 45, 60 seconds (one minute), two minutes, three minutes, four, or five minutes following application) after application of the active agent-containing formulation. Alternatively the hair may be rinsed, shampooed, or conditioned within about 60 minutes following application of the first and second formulations, within about 45 minutes following application, between about 5 minutes and about 20 minutes, or about 10 minutes after the final application of the active agent formulation to the hair, depending on the hair type. In some embodiments of the methods described herein, the treated hair is washed, rinsed, shampooed, or conditioned about 45 minutes after the application of the relaxing and active agent formulations, when they are applied simultaneously. In some embodiments of the methods described herein, the treated hair is washed, rinsed, shampooed, or conditioned about 15 minutes after the application of an active agent formulation, when the active formulation is applied immediately (i.e., within about 5, 10, 15, 20, 25, 30, 35, 40, 45, 50, 55, 60 seconds (one minute), two minutes, three minutes, four, or five minutes) after applying the relaxing agent formulation.

Alternately, the hair may be washed, rinsed, shampooed, or conditioned and a subsequent application of the active agent formulation may be applied which does not have to be washed or rinsed from the hair.

The active agent(s) can covalently react with thiols present in the relaxed hair and the thiols remain crosslinked for at least one week, preferably for at least one month following application of the active agent. The thiols may remain crosslinked for longer periods of time, such as for about three months or greater than three months, such as for at least one year following application of the active agent. The reaction is a stable reaction, such that the thiols remain crosslinked even if subjected to a hair coloring treatment (simultaneous or subsequent to the relaxing process).

EXAMPLES

Example 1

Controlled Relaxing of Hair Using Bismaleate Active Agent in Combination with a Hydroxide-Containing Relaxer General Hair samples were obtained from a human subject and cut in ½ inch wide wefts.

Relaxing agents: Mizani® Rhelaxer normal strength.

Active agent-containing relaxing formulation: One ounce of the commercial hydroxide formulation was further mixed with a liquid solution containing 0.25 ounces of a formulation having 20 weight percent of 2,2'-(ethane-1,2-diylbis(oxy))bis(ethan-1-amine) di-maleate as the active agent.

Methods

The active agent-containing relaxation formulation was brushed into the hair sample and left for 45 minutes with periodic combing. The solution was subsequently washed with shampoo, conditioned, and allowed to dry.

Results

The combination of the active agent and hydroxide (lye) relaxer produced relaxed hair that had more curl than a control (relaxing formulation which contains no active agent). The appearance and texture of the relaxed hair treated with a combination of the lye-based relaxing agent and active agent formulation demonstrated much improved hair conditioning (stronger, improved feel, softer with lower porosity), as compared to the control.

Example 2

Controlled Relaxing of Hair Using Bismaleate Active Agent in Combination with a Hydroxide-Containing Relaxer General Hair samples were obtained from a human subject and cut in ½ inch wide wefts.

Relaxing agents: Mizani® Rhelaxer normal strength.

Active agent-containing relaxing formulation: One ounce of the commercial hydroxide formulation was further mixed with a liquid solution containing 0.125 ounces of a formulation having 20 weight percent of 2,2'-(ethane-1,2-diylbis(oxy))bis(ethan-1-amine) di-maleate as the active agent.

Methods

The active agent-containing relaxation formula was brushed into the hair sample and left for 45 minutes with periodic combing. The hair was then washed with shampoo, conditioned, and allowed to dry.

Results

As compared to the formulation tested in Example 1, the combination of the active agent and hydroxide (lye) relaxer but which contained a reduced amount of the active agent produced relaxed hair that had less curl than in Example 1, but had more curl as compared to a control (relaxing agent which contains no active agent).

The appearance and texture of the relaxed hair treated with a combination of the lye-based relaxing agent and active agent formulation demonstrated much improved hair conditioning (stronger, improved feel, softer with lower porosity), as compared to the control.

Example 3

Controlled Relaxing of Hair using Maleic Acid as the Active Agent in Combination with a Hydroxide-Containing Relaxer General Hair samples were obtained from a human subject and cut in ½ inch wide wefts.

Relaxing agents: Mizani® Rhelaxer normal strength.

Active agent-containing relaxing formulation: One ounce of the commercial hydroxide formulation was further mixed with a liquid solution containing 0.25 ounces of a formulation having 10 weight percent of maleic acid as the active agent.

Methods

The active agent-containing relaxation formulation was brushed into the hair sample and left for 45 minutes with periodic combing. The solution was subsequently washed with shampoo, conditioned, and allowed to dry.

Results

The combination of the active agent and hydroxide (lye) relaxer resulted in relaxed hair that had more curl than a control (relaxing formulation that contained no active agent). The appearance and texture of the relaxed hair treated with a combination of the lye-based relaxing agent and active agent formulation demonstrated much improved hair conditioning (stronger, improved feel, softer with lower porosity), as compared to the control.

Example 4

Treating Lye Relaxed Hair Using a Bismaleate Active Agent

General

Hair samples were obtained from a human subject and cut in ½ inch wide wefts.

Relaxing agents: Mizani® Rhelaxer normal strength.

Active agent formulation: A 0.5 ounce formulation of 20 weight percent of 2,2'-(ethane-1,2-diylbis(oxy))bis(ethan-1-amine) di-maleate as the active agent was prepared in water (3 ounces).

Methods

The commercial relaxation formula was brushed into the hair sample and left for 45 minutes with periodic combing. The hair was then washed with shampoo, conditioned, and allowed to dry.

The active agent formula was then applied to the dried, relaxed hair and allowed to stand for 15 minutes. The hair was then washed with shampoo, conditioned, and allowed to dry.

Results

The appearance and texture of hair which was first treated with a lye-based relaxing agent and subsequently treated with an active agent formulation demonstrated much improved hair conditioning (stronger, improved feel, with lower porosity), as compared to the control. After the treatment, some of the original curl returned to the hair as compared to the hair immediately after lye-relaxation without the use of an active agent.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for achieving a desired level of curl in hair comprising:
   (a) applying to the hair one or more relaxing agents at an alkaline pH, wherein at least one of the relaxing agents is an alkali metal containing hydroxide; and
   (b) applying to the hair an active agent of Formula II:

$$(B)_m\text{—}Z\text{-}(A)_n \qquad \text{Formula II}$$

wherein Z is a linker or is absent and the linker is not a polymer;

m and n are each an integer independently selected from 1-6, and the sum of m+n is equal to or greater than 2;

B is a functional group capable of forming a covalent bond with a nucleophile, and B is independently selected from the group consisting of:

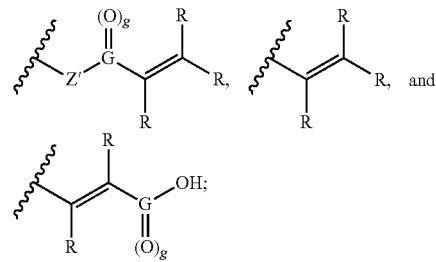

wherein R is independently selected from the group consisting of hydrogen, $C_{1-6}$ alkyl groups, aryl groups, or an ionizable functional groups and Z' is oxygen (O), NH or is absent, and G is carbon (C) and g is 1, or G is sulfur (S) and g is 2;

A is an ionizable functional group independently selected from the group consisting of: —COOH, —$SO_3H$, —$PO_3H_2$, —$N(R^1)_2$, —$N(R^1)_3$; wherein $R^1$ is independently selected from the group consisting of a hydrogen, alkyl, alkenyl, alkynyl, cycloalkyl, aryl, heterocycloalkyl and heteroaryl groups; wherein each $R^1$ is independently unsubstituted or substituted with one or more substituents; wherein the one or more relaxing agents cause the hair to relax;

wherein the active agent is present in an effective amount to retain a level of curl (percent curl retention) in the treated hair in the range of about 0-99%, compared to the amount of curl in the hair prior to step (a); and wherein steps (a) and (b) are performed simultaneously.

2. The method of claim 1, wherein the one or more relaxing agents and the active agent are mixed to form a mixture prior to application to the hair.

3. The method of claim 2, wherein the active agent is present in an amount ranging from about 0.01 wt % to about 50 wt % of the mixture.

4. The method of claim 2, wherein the active agent is present in an amount ranging from about 0.1 wt % to about 50 wt % of the mixture.

5. The method of claim 2, wherein the active agent is present in an amount ranging from about 0.1 wt % to about 5 wt % of the mixture.

6. The method of claim 2, wherein the active agent is present in an amount ranging from about 1 wt % to about 5 wt % of the mixture.

7. The method of claim 1, wherein the one or more relaxing agents are provided in a first formulation and wherein the active agent is provided in a second formulation, wherein the weight ratio of the first formulation to the second formulation is about 10:1 to about 1:1.

8. The method of claim 1, wherein the level of curl retained is about 5, 10, 15, 20, 25, 30, 35, 40, 45, 50, 55, 60, 65, 70, or 75%, or more of the curl in the hair prior to step (a).

9. The method of claim 1, wherein the alkali metal containing hydroxide is selected from the group consisting of sodium hydroxide, lithium hydroxide, and potassium hydroxide.

10. The method of claim 1, further comprising,
(c) rinsing, shampooing, and/or conditioning the hair, wherein step (c) occurs subsequent to step (b).

11. The method of claim 1, wherein the active agent is selected from the group consisting of:

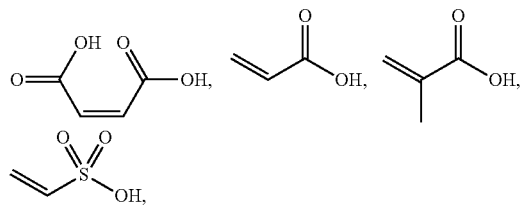

or simple salts thereof.

12. The method of claim 1, wherein the percent curl retention is between 0% and 10%.

13. The method of claim 1, wherein the percent curl retention is greater than 50%.

14. The method of claim 1, wherein the percent curl retention is determined according to Equation 1:

Percent Curl Retention=$(L_{ext}-L_f)/(L_{ext}-L_i) \times 100$     (Eq. 1)

where $L_{ext}$ is the length of hair prior to steps (a) and (b) when fully extended, $L_f$ is the final, non-extended length of the hair following a steps (a) and (b), and $L_i$ is the initial length of hair in its non-extended state, and wherein $L_{ext}$ does not equal $L_i$.

15. The method of claim 1, wherein the effective amount of active agent is lower for lower percent curl retention values compared to the effective amount of active agent for greater percent curl retention values.

16. A method for achieving a desired level of curl in hair comprising:
(a) applying to the hair one or more relaxing agents at an alkaline pH, wherein at least one of the relaxing agents is an alkali metal containing hydroxide; and
(b) applying to the hair an active agent wherein the active agent has the formula:

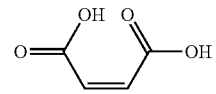

or salts thereof; wherein the one or more relaxing agents cause the hair to relax;
wherein the active agent is present in an effective amount to retain a level of curl (percent curl retention) in the treated hair in the range of about 0-99%, compared to the amount of curl in the hair prior to step (a); and
wherein steps (a) and (b) are performed simultaneously.

17. The method of claim 16, wherein the one or more relaxing agents and the active agent are mixed to form a mixture prior to application to the hair.

18. The method of claim 17, wherein the active agent is present in an amount ranging from about 0.01 wt % to about 50 wt % of the mixture.

19. The method of claim 17, wherein the active agent is present in an amount ranging from about 0.1 wt % to about 50 wt % of the mixture.

20. The method of claim 17, wherein the active agent is present in an amount ranging from about 0.1 wt % to about 5 wt % of the mixture.

21. The method of claim 17, wherein the active agent is present in an amount ranging from about 1 wt % to about 5 wt % of the mixture.

22. The method of claim 16, wherein the one or more relaxing agents are provided in a first formulation and wherein the active agent is provided in a second formulation, wherein the weight ratio of the first formulation to the second formulation is about 10:1 to about 1:1.

23. The method of claim 16, wherein the level of curl retained is about 5, 10, 15, 20, 25, 30, 35, 40, 45, 50, 55, 60, 65, 70, or 75%, or more of the curl in the hair prior to step (a).

24. The method of claim 16, wherein the alkali metal containing hydroxide is selected from the group consisting of sodium hydroxide, lithium hydroxide, and potassium hydroxide.

25. The method of claim 16, further comprising,
(c) rinsing, shampooing, and/or conditioning the hair, wherein step (c) occurs subsequent to step (b).

26. The method of claim 16, wherein the percent curl retention is between 0% and 10%.

27. The method of claim 16, wherein the percent curl retention is greater than 50%.

28. The method of claim 16, wherein the percent curl retention is determined according to Equation 1:

Percent Curl Retention=$(L_{ext}-L_f)/(L_{ext}-L_i) \times 100$     (Eq. 1)

where $L_{ext}$ is the length of hair prior to steps (a) and (b) when fully extended, $L_f$ is the final, non-extended length of the hair following a steps (a) and (b), and $L_i$ is the initial length of hair in its non-extended state, and wherein $L_{ext}$ does not equal $L_i$.

29. The method of claim 16, wherein the amount of active agent is lower for lower percent curl retention values compared to the amount of active agent for greater percent curl retention values.

* * * * *

UNITED STATES PATENT AND TRADEMARK OFFICE
CERTIFICATE OF CORRECTION

PATENT NO. : 9,597,273 B2
APPLICATION NO. : 15/137788
DATED : March 21, 2017
INVENTOR(S) : Eric D. Pressly and Craig J. Hawker It is certified that error appears in the above-identified patent and that said Letters Patent is hereby corrected as shown below:

In the Specification

Column 5, Line 42; replace "heterocyclic ring" with --heterocyclic rings--.
Column 6, Line 49; replace "aminoacid" with --amino acid--.
Column 7, Line 42; replace "from about from about" with --from about--.
Column 7, Line 50; replace "at pH of" with --at a pH of--.
Column 8, Line 47; replace "bound" with --bind--.
Column 10, Line 67; replace "$(B)_m$—Z-$(A)_n$" with -- 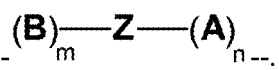 --.
Column 12, Lines 23-24; replace "such a dicarboxylic acids" with --such a dicarboxylic acid--.
Column 14, Lines 27-28; replace "such a dicarboxylic acids" with --such a dicarboxylic acid--.
Column 15, Line 14; replace "to about to about" with --to about--.
Column 15, Line 51; replace "behenamide, behenamide" with --behenamide--.
Column 17, Line 34; replace "contains" with --contain--.
Column 18, Line 55; please replace the term "producing" with --produce--.
Column 22, Line 45; replace "is is" with --is--.
Column 25, Lines 41-42; replace "2,2'-(ethane-1,2-diylbis(oxy))bis(ethan-1-amine)" with --2,2'-(ethane-1,2-diylbis(oxy))bis(ethane-1-amine)--.

In the Claims

Claim 1, Column 26, Line 15; replace "$(B)_m$—Z-$(A)_n$" with -- 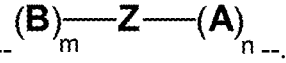 --.
Claim 1, Column 26, Lines 38-39; replace "or an ionizable functional groups" with --and ionizable functional groups--.
Claim 11, Column 27, Line 29; replace " 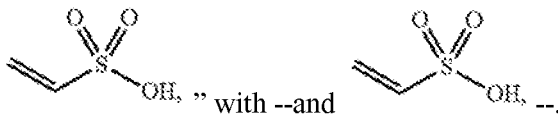 " with --and (same structure)--.
Claim 14, Column 27, Line 46; replace "following a steps" with --following steps--.
Claim 28, Column 28, Line 52; replace "following a steps" with --following steps--.

Signed and Sealed this
Twenty-eighth Day of November, 2017

Joseph Matal
*Performing the Functions and Duties of the
Under Secretary of Commerce for Intellectual Property and
Director of the United States Patent and Trademark Office*

Claim 29, Column 28, Line 55; replace "wherein the amount" with --wherein the effective amount--.
Claim 29, Column 28, Line 57; replace "to the amount" with --to the effective amount--.